United States Patent
Hennings et al.

(10) Patent No.: US 7,921,854 B2
(45) Date of Patent: *Apr. 12, 2011

(54) ENDOVENOUS LASER TREATMENT FOR VARICOSE VEINS

(75) Inventors: David R. Hennings, Roseville, CA (US); Mitchel P. Goldman, San Diego, CA (US); Robert A. Weiss, Hunt Valley, MD (US); Eric B. Taylor, Roseville, CA (US); Don Johnson, Roseville, CA (US)

(73) Assignee: CoolTouch Incorporated, Roseville, CA (US)

( * ) Notice: Subject to any disclaimer, the term of this patent is extended or adjusted under 35 U.S.C. 154(b) by 753 days.

This patent is subject to a terminal disclaimer.

(21) Appl. No.: 11/562,944

(22) Filed: Nov. 22, 2006

(65) Prior Publication Data

US 2007/0123846 A1 May 31, 2007

Related U.S. Application Data

(63) Continuation-in-part of application No. 10/699,212, filed on Oct. 30, 2003, and a continuation-in-part of application No. 10/982,504, filed on Nov. 4, 2004, now Pat. No. 7,524,316, which is a continuation-in-part of application No. PCT/US03/35178, filed on Oct. 30, 2003.

(60) Provisional application No. 60/422,566, filed on Oct. 31, 2002.

(51) Int. Cl.
*A61B 19/00* (2006.01)

(52) U.S. Cl. ............... 128/898; 606/3; 606/7; 606/15; 607/88; 607/89

(58) Field of Classification Search ............... 606/3, 7, 606/13–16; 607/88–92, 96, 100; 128/898
See application file for complete search history.

(56) References Cited

U.S. PATENT DOCUMENTS

| | | | |
|---|---|---|---|
| 4,233,991 | A | 11/1980 | Bradley et al. |
| 4,854,320 | A | 8/1989 | Dew et al. |
| 4,899,741 | A | 2/1990 | Bentley et al. |
| 5,022,399 | A | 6/1991 | Biegeleisen |
| 5,196,004 | A | 3/1993 | Slinofsky |
| 5,207,672 | A | 5/1993 | Roth et al. |
| 5,707,403 | A | 1/1998 | Grove et al. |
| 5,789,755 | A | 8/1998 | Bender |
| 5,810,801 | A | 9/1998 | Anderson et al. |

(Continued)

FOREIGN PATENT DOCUMENTS

WO WO-92-17243 10/1992

(Continued)

OTHER PUBLICATIONS

U.S. Appl. No. 10/335,176, filed Dec. 2002, Baumgardner et al.

(Continued)

*Primary Examiner* — Ahmed M Farah
(74) *Attorney, Agent, or Firm* — Ray K. Shahani, Esq.; Kin H. Lai

(57) ABSTRACT

Improved devices and methods for removing blood from a blood vessel in preparation for endovenous laser ablation are described. The improved methods include one or more of: placing the patient in the Trendelenburg position, applying external compression around the vein, massaging the vein, cooling the vein externally, encouraging spasming of the vein, and removing blood with a suction device.

26 Claims, 9 Drawing Sheets

U.S. PATENT DOCUMENTS

| | | | |
|---|---|---|---|
| 5,820,626 A | 10/1998 | Baumgardner et al. | |
| 5,824,005 A | 10/1998 | Motamedi et al. | |
| 5,885,274 A | 3/1999 | Fullmer et al. | |
| 5,968,034 A | 10/1999 | Fullmer et al. | |
| 5,976,123 A | 11/1999 | Baumgardner et al. | |
| 5,984,915 A | 11/1999 | Loeb et al. | |
| 6,014,589 A | 1/2000 | Farely et al. | |
| 6,028,316 A | 2/2000 | Bender | |
| 6,033,398 A | 3/2000 | Farley et al. | |
| 6,083,223 A | 7/2000 | Baker | |
| 6,117,335 A | 9/2000 | Bender | |
| 6,135,997 A | 10/2000 | Laufer et al. | |
| 6,139,527 A | 10/2000 | Laufer et al. | |
| 6,176,854 B1 | 1/2001 | Cone | |
| 6,197,020 B1 | 3/2001 | O'Donnell, Jr. | |
| 6,200,332 B1 | 3/2001 | Del Giglio | |
| 6,200,466 B1 | 3/2001 | Bender et al. | |
| 6,206,873 B1 | 3/2001 | Paolini et al. | |
| 6,224,593 B1 | 5/2001 | Ryan et al. | |
| 6,228,078 B1 | 5/2001 | Eggers et al. | |
| 6,258,084 B1 | 7/2001 | Goldman et al. | |
| 6,263,248 B1 | 7/2001 | Farley et al. | |
| 6,270,476 B1 | 8/2001 | Santoianni et al. | |
| 6,273,883 B1 | 8/2001 | Furumoto | |
| 6,273,885 B1 | 8/2001 | Koop et al. | |
| 6,290,675 B1 | 9/2001 | Vuianic et al. | |
| 6,306,130 B1 * | 10/2001 | Anderson et al. | 606/27 |
| 6,346,105 B1 | 2/2002 | Tu et al. | |
| 6,361,496 B1 | 3/2002 | Zikorus et al. | |
| 6,398,777 B1 * | 6/2002 | Navarro et al. | 606/7 |
| 6,413,253 B1 | 7/2002 | Koop et al. | |
| 6,451,007 B1 | 9/2002 | Koop et al. | |
| 6,451,044 B1 | 9/2002 | Naghavi et al. | |
| 6,520,975 B2 | 2/2003 | Branco | |
| 6,626,899 B2 | 9/2003 | Houser et al. | |
| 6,638,273 B1 | 10/2003 | Farley et al. | |
| 6,761,826 B2 | 7/2004 | Bender et al. | |
| 6,986,766 B2 * | 1/2006 | Caldera et al. | 606/15 |
| 7,160,289 B2 * | 1/2007 | Cohen | 606/9 |
| 7,273,478 B2 * | 9/2007 | Appling et al. | 606/15 |
| 7,524,316 B2 * | 4/2009 | Hennings et al. | 606/7 |
| 2004/0010248 A1 | 1/2004 | Appling et al. | |
| 2004/0092913 A1 * | 5/2004 | Hennings et al. | 606/3 |

FOREIGN PATENT DOCUMENTS

| | | |
|---|---|---|
| WO | WO-93-15664 | 8/1993 |

OTHER PUBLICATIONS

U.S. Appl. No. 10/351,273, filed Jan. 2003, Hennings et al.
U.S. Appl. No. 10/699,212, filed Oct. 2003, Hennings et al.
U.S. Appl. No. 08/631,800, filed Apr. 1996, Hennings et al.
U.S. Appl. No. 10/738,384, filed Dec. 2003, Hennings et al.
U.S. Appl. No. 11/131,577, filed May 2005, Hennings et al.
U.S. Appl. No. 09/185,490, filed Jul. 2000, Koop et al.
U.S. Appl. No. 09/135,330, filed Jul. 1998, Koop et al.
U.S. Appl. No. 09/134,776, filed Aug. 1998, Koop et al.
U.S. Appl. No. 10/160,579, filed May 2002, Koop et al.
U.S. Appl. No. 10/031,154, filed Jan. 2005, Koop et al.
U.S. Appl. No. 08/482,208, filed Jun. 1995, Hennings et al.
U.S. Appl. No. 11/612,324, filed Dec. 18, 2006, Hennings et al.
Jacques; Skin Optics; Oregon Medical Laser Cent News; http://omIc.ogi.edu/news/jan98/skinoptics.html; Jan. 1998; 8 pages.
Chang et al.; Endovenous Laser Photocoagulation (EVLP) for Varicose Veins; Lasers in Surgery and Medicine 31:257-262 (2002); 6 pages.
Weiss et al.; Endovenous Closure of the Greater Saphenous Vein with Radio-frequency or Laser; Cosmetic Surgery Text 2003; 26 pages.
Weiss et al.: Controlled Radiofrequency Endovenous Occlusion Using a Radiofrequency Catheter Under Duplex Guidance to Eliminate Saphenous Varicose VeinUnique Reflux: A 2-Year Follow Up: American Society for Dermatologic Surgery, Inc. 2002: 5 pages.
Goldman et al.; Intravascular 1320nm Laser Closure of the Great Saphenous Vein: A 6-12 Month Follow-up Study; Dermatology/Cosmelic Laser Associates of La Jolla, Inc.; 28 pages.
Goldman: Endovenous Nd: YAG 1320nm Laser Treatment of the Greater Saphenous Vein: A Preliminary Study on 12 legs; Dermatology/Cosmetic Laser Associates of La Jolla, Inc.; 15 pa.
Goldman et al.; Endovenous 1064-nm and 1320-nm Nd:YAG Laser Treatment of the Porcine Greater Saphenous Vein; Cosmetic Dermatology; Feb. 2003; 4 pages.

* cited by examiner

ENDOVENOUS LASER TREATMENT FOR VARICOSE VEINS

RELATED APPLICATION

This Application is continuation-in-part of pending U.S. application Ser. No. 10/699,212 filed Oct. 30, 2003, entitled "ENDOVENOUS CLOSURE OF VARICOSE VEINS WITH MID INFRARED LASER", which application claims the benefit of U.S. Provisional Patent Application Ser. No. 60/422,566 filed Oct. 31, 2002, entitled "ENDOVENOUS CLOSURE OF VARICOSE VEINS WITH MID INFRARED LASER", each of which applications is incorporated herein by reference in its entirety. This Application is also a continuation-in-part of U.S. patent application Ser. No. 10/982,504, filed on Nov. 4, 2004, and titled "ENDOVENOUS CLOSURE OF VARICOSE VEINS WITH MID INFRARED LASER", which application is a continuation-in-part of and claims the benefit of International Application Number PCT/US2003/035178, filed under the Patent Cooperation Treaty on Oct. 30, 2003, entitled "ENDOVENOUS CLOSURE OF VARICOSE VEINS WITH MID INFRARED LASER", designating the United States of America, and titled "ENDOVENOUS CLOSURE OF VARICOSE VEINS WITH MID INFRARED LASER", which application claims the benefit of U.S. Provisional Patent Application Ser. No. 60/422,566 filed Oct. 31, 2002, entitled "ENDOVENOUS CLOSURE OF VARICOSE VEINS WITH MID INFRARED LASER", each of which applications is incorporated herein by reference in its entirety.

FIELD OF THE INVENTION

The present invention relates generally laser assisted method and apparatus for treatment of varicose veins and, more particularly, to improved methods for preparing a patient to undergo endovenous laser ablation procedures.

BACKGROUND OF THE INVENTION

Most prior techniques to treat varicose veins have attempted to heat the vessel by targeting the hemoglobin in the blood and then having the heat transfer to the vessel wall. Lasers emitting wavelengths of 500 to 1100 nm have been used for this purpose from both inside the vessel and through the skin. Attempts have been made to optimize the laser energy absorption by utilizing local absorption peaks of hemoglobin at 810, 940, 980 and 1064 nm. RF technology has been used to try to heat the vessel wall directly but this technique requires expensive and complicated catheters to deliver electrical energy in direct contact with the vessel wall. Other lasers at 810 nm and 1.06 um have been used in attempts to penetrate the skin and heat the vessel but they also have the disadvantage of substantial hemoglobin absorption which limits the efficiency of heat transfer to the vessel wall, or in the cases where the vessel is drained of blood prior to treatment of excessive transmission through the wall and damage to surrounding tissue. All of these prior techniques result in poor efficiency in heating the collagen in the wall and destroying the endothelial cells.

For example, Navarro et al., U.S. Pat. No. 6,398,777, issued Jun. 4, 2002, teaches that it is necessary to have at least some blood in the vein to absorb Diode laser radiation to perform endovenous ablation. More recently, Navarro teaches to remove a significant amount of blood but to leave a layer in the vein to act as an absorbing chromophore for the laser. These lasers in fact will not perform laser ablation of the vein walls with a completely blood free vein.

Goldman et al., in U.S. Pat. No. 6,752,803, issued Jun. 22, 2004, teach the removal of blood with the use of tumescent anesthesia to compress the vein prior to laser treatment. This method has the disadvantage of not completely removing blood from the vessel. It is generally accepted within the art that the most compression that tumescent anesthesia can accomplish is to bring the vessel to about 5 mm in diameter. At this size, a significant amount of blood can remain in the vessel. In fact, since tumescent anesthesia will only compress the vein to a controlled size, the use of tumescent anesthesia has proven to be an excellent way to leave a precisely controlled amount of blood in the vein to act as an absorbing chromophore for hemoglobin targeting lasers such as the 810, 940 and 980 nm diode systems.

On the other hand, recent attention has been paid to endovenous laser ablation techniques using lasers operating at wavelengths that do not require the presence of blood in the vein. For example, Hennings et al., in U.S. Patent Publication No. 2005/0131400, published on Jun. 16, 2005, teaches that lasers operating at wavelengths of from about 1200 nm to about 1800 nm produce laser energy that is more strongly absorbed by the vessel walls than by the blood, in comparison to the lasers operating at lower wavelengths. Accordingly, the lasers and laser ablation techniques described by Hennings will actually operate better when the vein is drained as far as possible.

Regardless of the endovenous laser treatment method used, any blood remaining in the vessel also has the potential of creating additional problems. For example, depending upon the laser system components and their operating parameters, the blood that remains in the vein may coagulate when heated by the laser and cause thrombosis, non closures, or pain and bruising. In addition, small pockets of blood act as heat sinks during the laser treatment and need to be heated to coagulation temperatures in order to adequately ablate the vein wall. One milliliter of blood can absorb close to one joule of energy to raise its temperature one degree Celsius. Since the damage temperature of the vein wall is around 80 degrees C., it could take as much as 50 Joules of energy to raise this small pocket of blood from 30 deg C. The laser treatment dosage is typically only 70 to 80 Jules per centimeter of vein length, so a one milliliter pocket of blood could absorb all of the energy intended to ablate the vein wall in that area leading to a section of non closure of the vein.

Furthermore, if the vein wall is perforated during ablation with blood present, blood may leak out of the vein causing bruising and discoloration of the skin post op.

Still further, during vein ablation, while the vein is shrinking to complete closure, blood left in the vein is squeezed out of the vein through the access point requiring sponging and absorbing pads to clean it up.

Blood will coagulate at about 80° C. Small pockets of blood that have coagulated and remain in the vein can prevent the vein from completely collapsing on itself. This residual thrombus prevents the opposing coagulated vein walls from touching during the healing process and prevents them from healing together. This is a major cause of non closures and failed procedures. Desmyttere et al. described the increased efficacy of endovenous ablation when using a 980 nm diode laser, and when the Trendelenburg position is used to drain the blood prior to treatment. See Jacques Desmyttere et al., "A 2 years follow-up study of endovenous 980 nm laser treatment of the great saphenous vein: Role of the blood content in the GSV," Elsevier, 19 Aug. 2005. They report closure rates of 91% after 2 years when blood is drained compared to closure of only 74% when the patient is in the horizontal position.

Finally, blood that is coagulated can be forced out of the vein into the remaining venous system and travel through the body as a deep vein thrombosis (DVT). This is a serious and potentially life threatening condition.

For these reasons, and for the reason that the mid infrared laser does not require a blood chromophore to convert laser energy into thermal energy, it would be desirable to have a method for more completely removing blood from the vein prior to endovenous ablation.

ADVANTAGES AND SUMMARY OF THE INVENTION

The present invention is directed to devices and methods for preparing a patient to undergo an endovenous laser ablation procedure. The subject devices and methods are intended to facilitate removal of blood from a vein or other vessel undergoing laser ablation prior to the actual ablation procedure. Removal of blood has been found to be beneficial to the patient, both in terms of increasing the efficacy of most laser ablation procedures, and in terms of increasing the safety of most laser ablation procedures.

The preparation method steps including the following:
- placing the patient in the Trendelenburg position, with the patient's feet elevated above the patient's head, thereby preventing blood from entering the vein after exsanguination;
- compressing the vein, preferably by applying a flexible bandage or other flexible wrap to the exterior of the leg of the patient;
- massaging the vein, either manually or with a suitable electronic medical device;
- cooling the vein, using any suitable cooling device such as an ice pack, ice wrap, or other external cooling device;
- causing the vein to spasm, such as by injection of a suitable vaso constrictor near the vein; and
- suctioning blood out of the vein, such as by connecting and operating a suction device to an access port of a sheath contained within the vein.

In a preferred embodiment, the patient is first given an injection of a femoral blocking anesthetic. After the anesthetic is administered, the venous blood removal procedures (described above) are implemented. After substantially all of the blood has been removed from the vein, all compression devices are removed, and tumescent anesthesia is injected along the vein to serve as a heat sink. One of any suitable endovenous laser treatment procedures is then performed.

Further details, objects and advantages of the present invention will be come apparent through the following descriptions, and will be included and incorporated herein.

DETAILED DESCRIPTION OF THE PREFERRED EMBODIMENT

Figure 1:
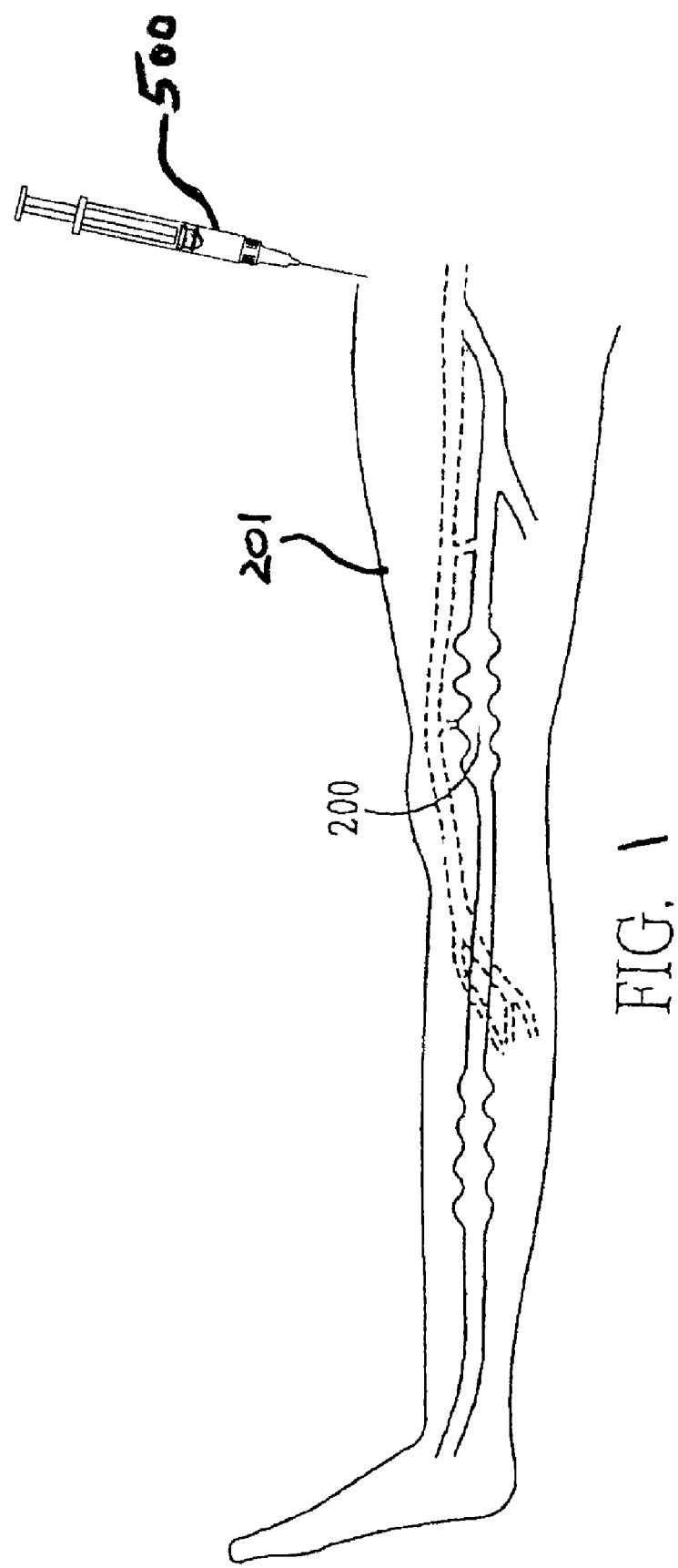
FIG. 1 is an illustration of a leg of a patient having varicosed veins 200 to be treated according to the methods and apparatus of the present invention.

The description that follows is presented to enable one skilled in the art to make and use the present invention, and is provided in the context of a particular application and its requirements. Various modifications to the disclosed embodiments will be apparent to those skilled in the art, and the general principles discussed below may be applied to other embodiments and applications without departing from the scope and spirit of the invention. Therefore, the invention is not intended to be limited to the embodiments disclosed, but the invention is to be given the largest possible scope which is consistent with the principles and features described herein.

It will be understood that in the event parts of different embodiments have similar functions or uses, they may have been given similar or identical reference numerals and descriptions. It will be understood that such duplication of reference numerals is intended solely for efficiency and ease of understanding the present invention, and are not to be construed as limiting in any way, or as implying that the various embodiments themselves are identical.

The methods for preparing a patient to undergo an endovenous laser ablation procedure are suitable for use with any endovenous laser ablation procedure, but the subject methods find particular application with those procedures for which substantially complete removal of blood from the vein is most beneficial. Several prior art endovenous laser ablation procedures are described above, including those taught by Navarro et al. (U.S. Pat. No. 6,398,777) and those taught by Goldman et al. (U.S. Pat. No. 6,752,803). Most preferred are the methods taught by Hennings et al. in U.S. Patent Publication No. 2005/0131400, and those taught by Hennings et al. in U.S. patent application Ser. No. 60/946,679, filed on behalf of the same assignee and on the same date as the present application. Each of the foregoing patents and publications is hereby incorporated by reference in its entirety.

The methods described herein are intended to remove as much blood as possible from the vein upon which the endovenous laser ablation procedure is to be applied. To that end, the following procedures are used.

Turning first to FIG. 1, a varicosed vein 200 to be subjected to an endovenous laser ablation procedure is shown in the leg 201 of the patient. A femoral blocking injection is used to provide anesthesia during the endovenous ablation. The laser ablation methods taught by Hennings et al. include use of the 1320 nm Nd:YAG laser, which has been shown to be much less painful than prior art devices, and which therefore allows the use of a less invasive single injection to block pain signals traveling along the femoral nerve instead of injecting large amounts of anesthesia all along the vein during a comparable tumescent procedure. In the preferred method, a 2 inch 22 gauge electrical nerve stimulator needle 500 may be inserted in the groin and the femoral nerve located with electrical stimulus. When the nerve is located, 10-15 ml of bupivacaine with epinephrine is injected to completely block sensation of pain from the lower extremities.

Figure 2:
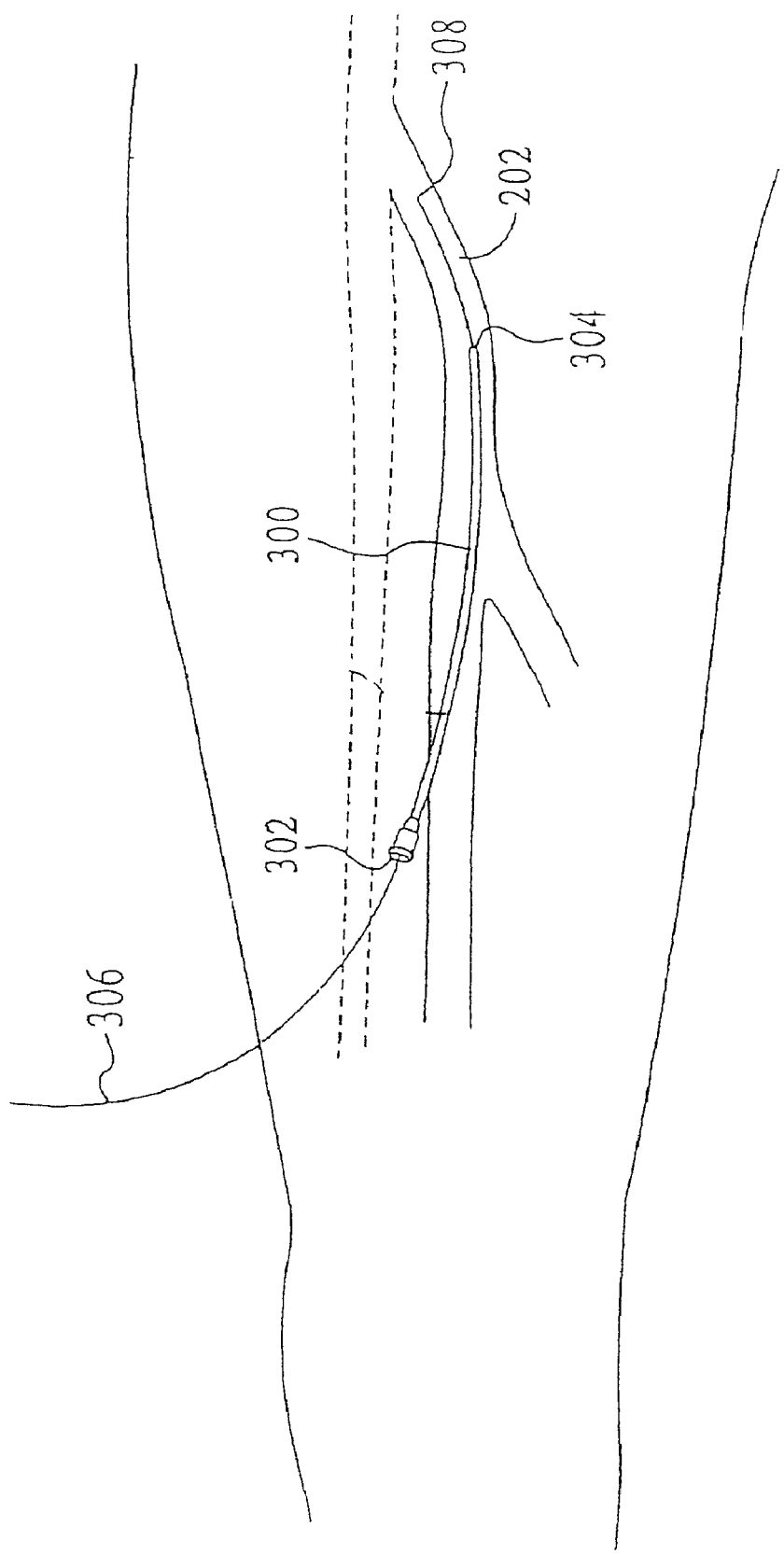
FIG. 2 is an illustration of the leg of a patient shown in FIG. 1, further showing the use of an introducer or dilator 300 with a laser fiber 306 passing through a lumen 302 of the dilator 300 and into the greater saphenous vein 202.

Next, as shown in FIG. 2, access to the vein is performed prior to draining the vein of blood. Once an access sheath is in place and the fiber is inserted into the vein, the vein can be drained without affecting the ability to get the fiber in position. An introducer sheath or dilator 300 is introduced into the vein by one of several techniques known to those skilled in the art. A quartz or sapphire optic fiber 306 is inserted through the lumen 302 of the introducer 300 and into the vein. Alternatively, the optic fiber 306 may be inserted directly into the vein 200 via a 16 gauge or similar sized needle, or through the vein 200 which has been externalized through a 2-3 mm incision with a phlebectomy hook (not shown). The fiber 306 is preferably from about 500 to about 600 μm in diameter, but fibers from about 50 μm or less to about 1 mm or more may be used. The optic fiber 306 includes an energy emitting tip 308 through which energy produced by the laser is emitted.

Once the access sheath 300 is in place, one or more of the following steps may be performed to drain the vein of blood. In a preferred method, all of the steps are performed. However, as explained more fully below, it is also contemplated that, for a given patient or a given set of circumstances, only one or any combination of two or more of these method steps may be performed in order to sufficiently drain the vein of blood. Although the steps are preferably performed in the order described below, alterations of the order of steps are also possible.

Figure 3:
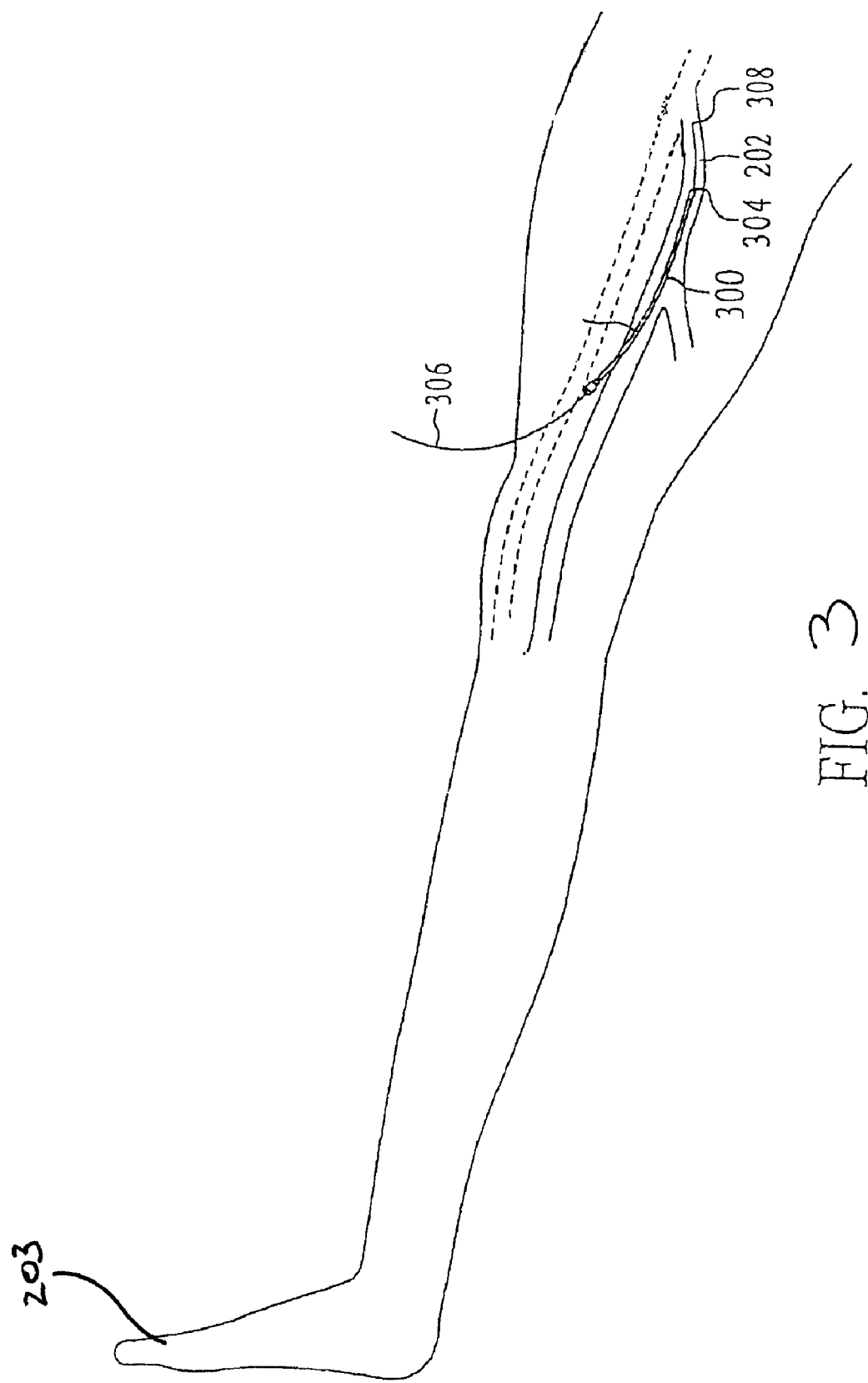
FIG. 3 is an illustration of the leg of a patient shown in FIG. 1, with the leg being positioned in the Trendelenburg position.

First, as illustrated in FIG. 3, the patient is placed in Trendelenburg position, in which the patient's feet 203 are positioned above the body. This position prevents new blood from entering the vein 202 when the vein is exsanguinated.

Figure 4:
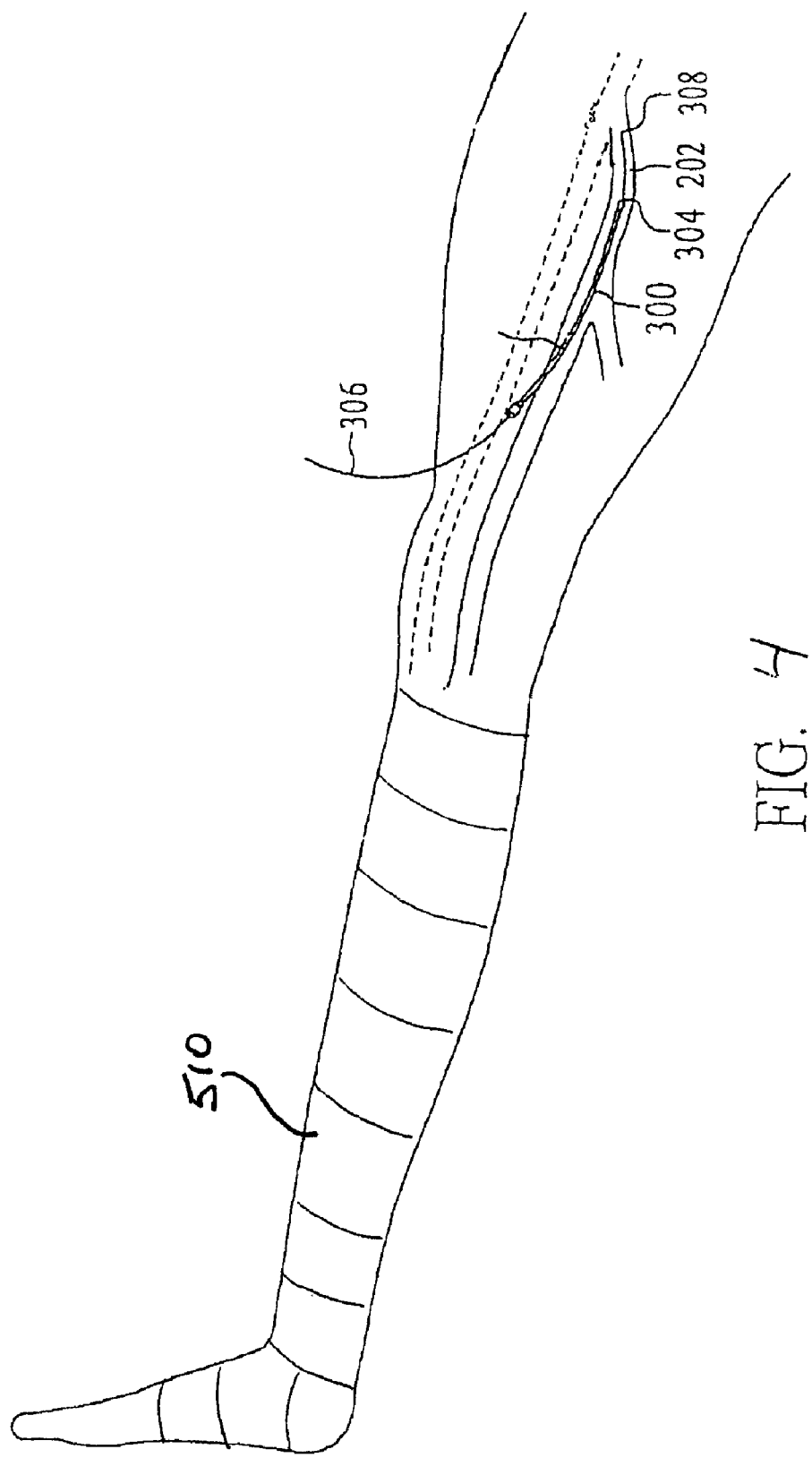
FIG. 4 is an illustration of the leg of a patient shown in FIG. 3, with a bandage or other wrap applied to the leg.

Next, as shown in FIG. 4, the leg is wrapped with a bandage or flexible wrap 510 to place external compression around the vein to force blood out. Although a bandage or flexible wrap 510 is preferred, the compression of the patient's leg may be applied using any method or device suitable for creating a compression around the vein that is the subject of the laser treatment procedure.

Figure 5:
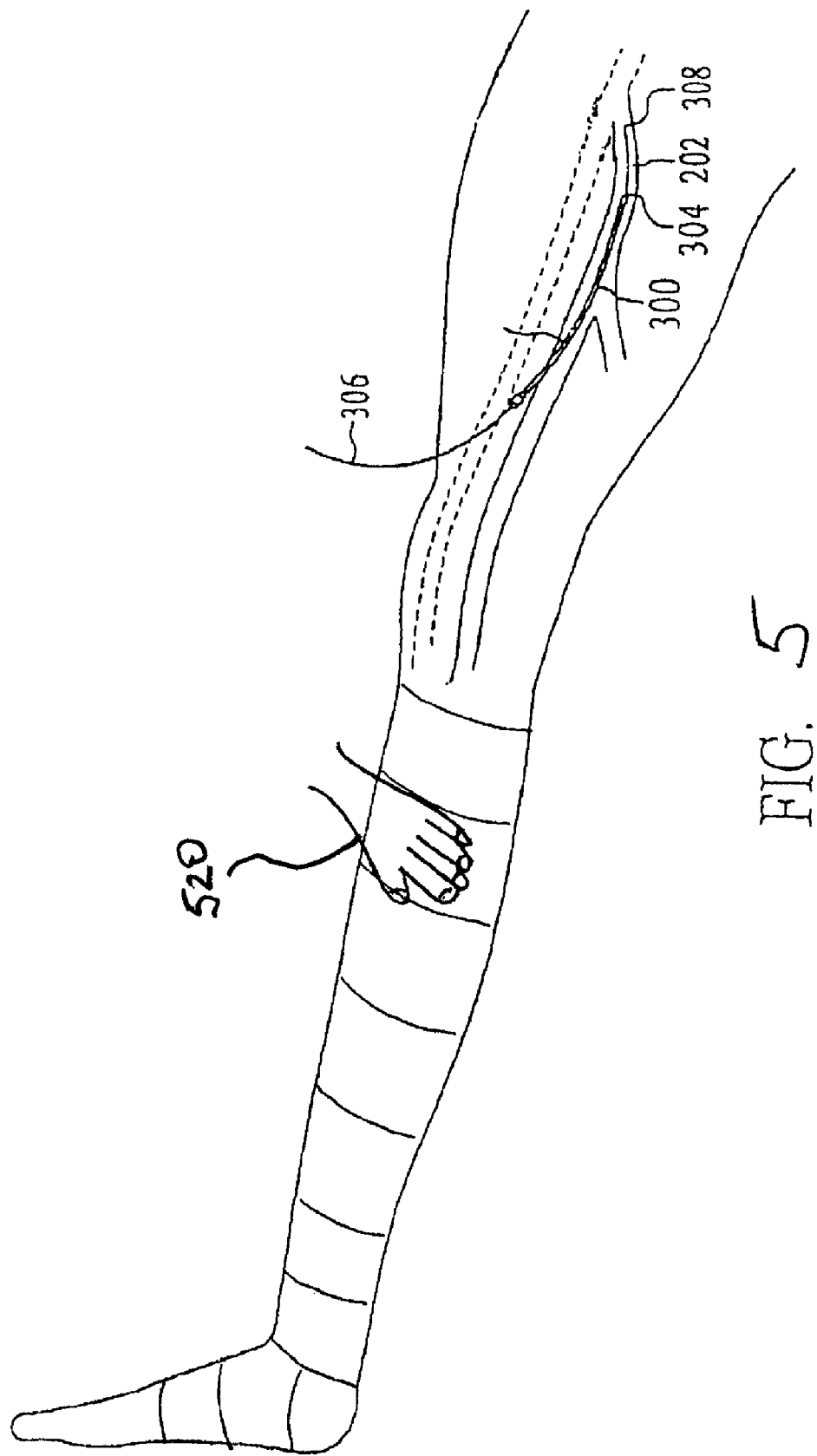
FIG. 5 is an illustration of the leg of a patient shown in FIG. 4 undergoing a manual massage.

Turning to FIG. 5, the vein is next massaged with hand pressure 520 to move blood out of the vein. Alternatively, any suitable mechanical massage device may be used to massage the vein such that blood is caused to move out of the vein.

Figure 6:
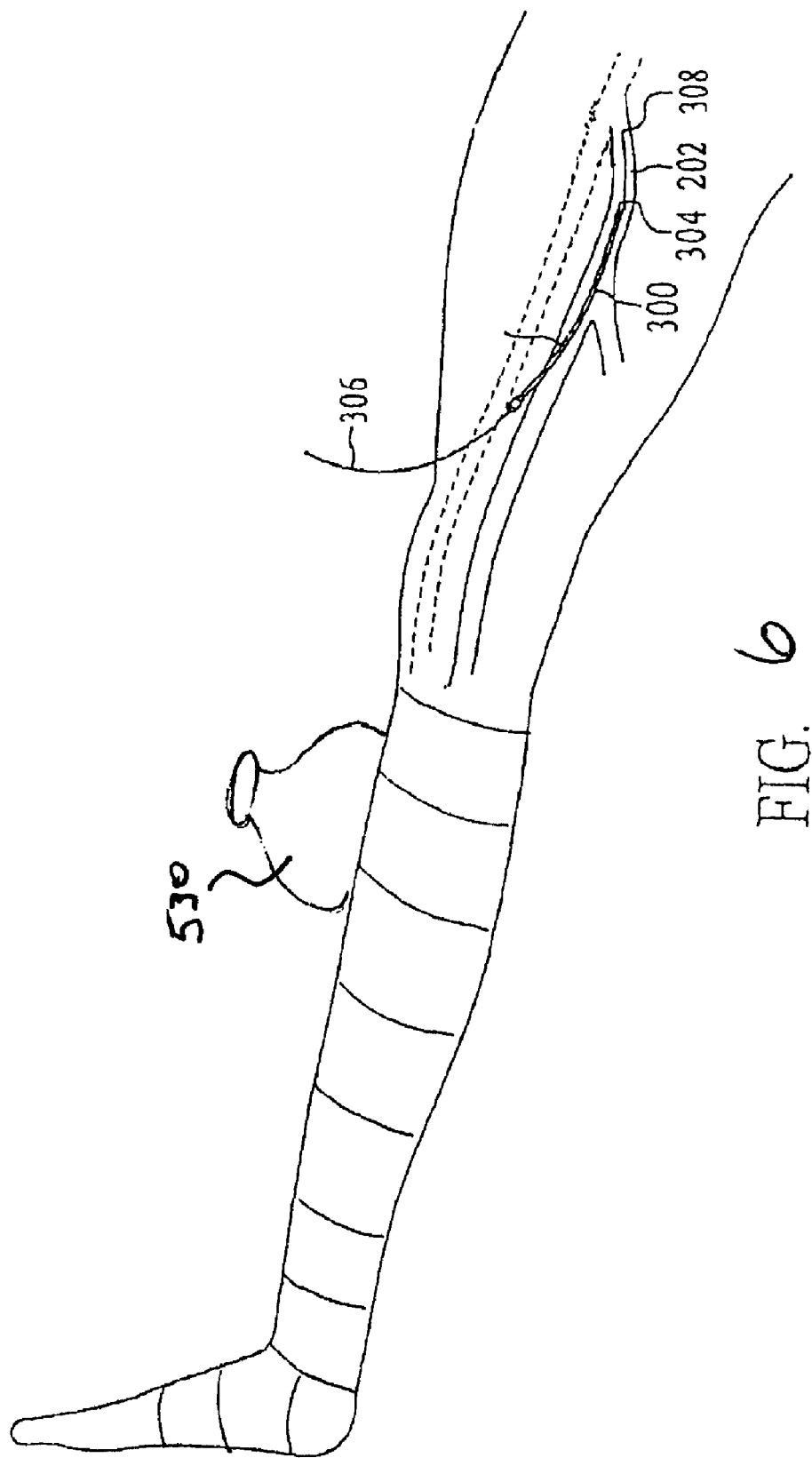
FIG. 6 is an illustration of the leg of a patient shown in FIG. 4, further including an ice pack for cooling.

Next, the leg is cooled from the exterior. FIG. 6 shows an ice pack 530 being applied to the leg. Any suitable mechanism or device for applying external cooling will be sufficient, including ice wraps or other external cooling devices.

Figure 7:
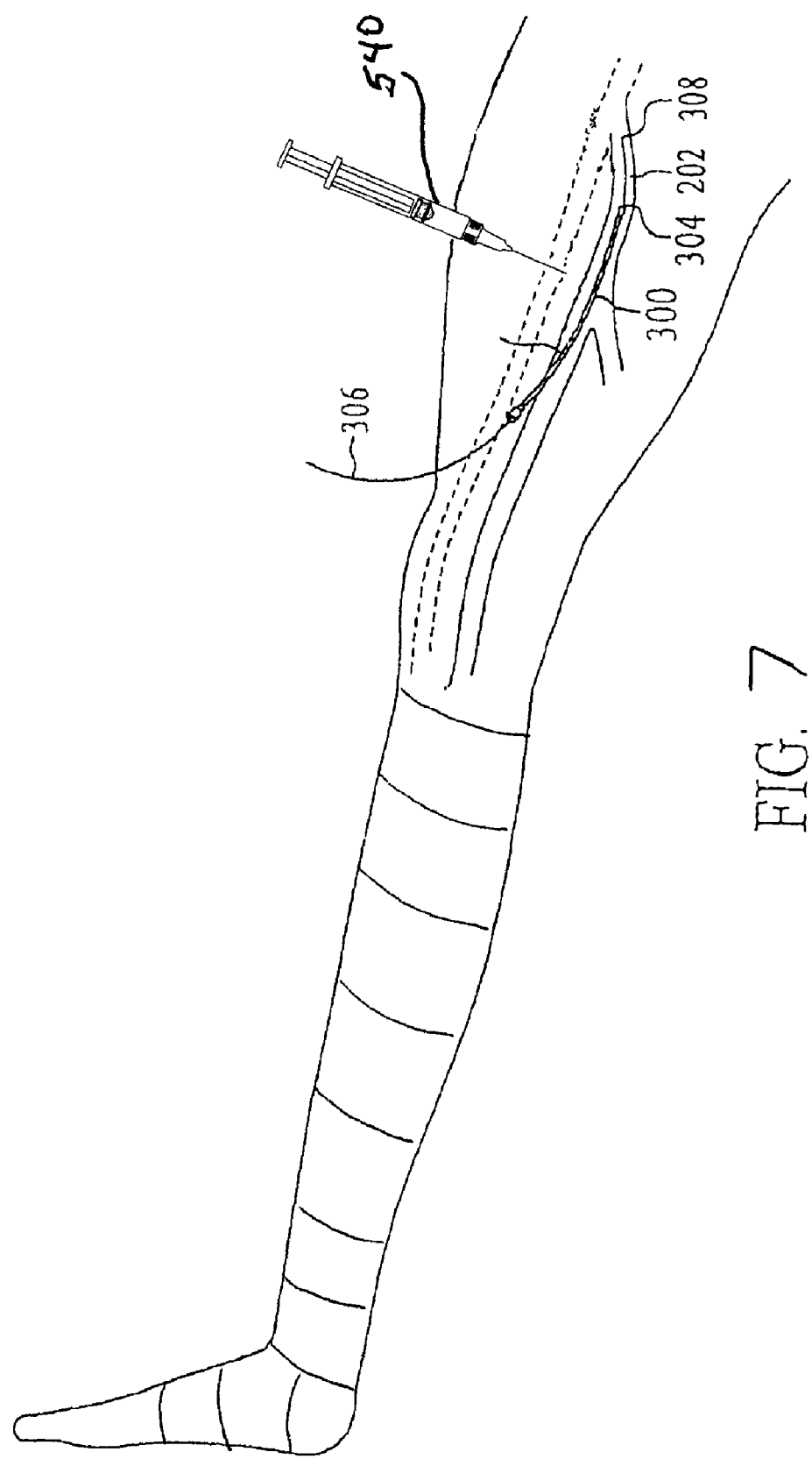
FIG. 7 is an illustration of the leg of a patient shown in FIG. 4, further illustrating the application by injection of a vaso constrictor.

Turning to FIG. 7, the next step includes causing the vein to spasm around the sheath 300. In the preferred method, a small amount of a vaso constrictor, such as ephinepherine, is injected via 30 gauge needle syringe 540 near the vein. It is preferable not to inject more than about 30 to 50 cc of the vaso constrictor. As the vein spasms around the sheath 300, it causes any remaining blood contained within the vein to be forced out of the vein.

Figure 8:
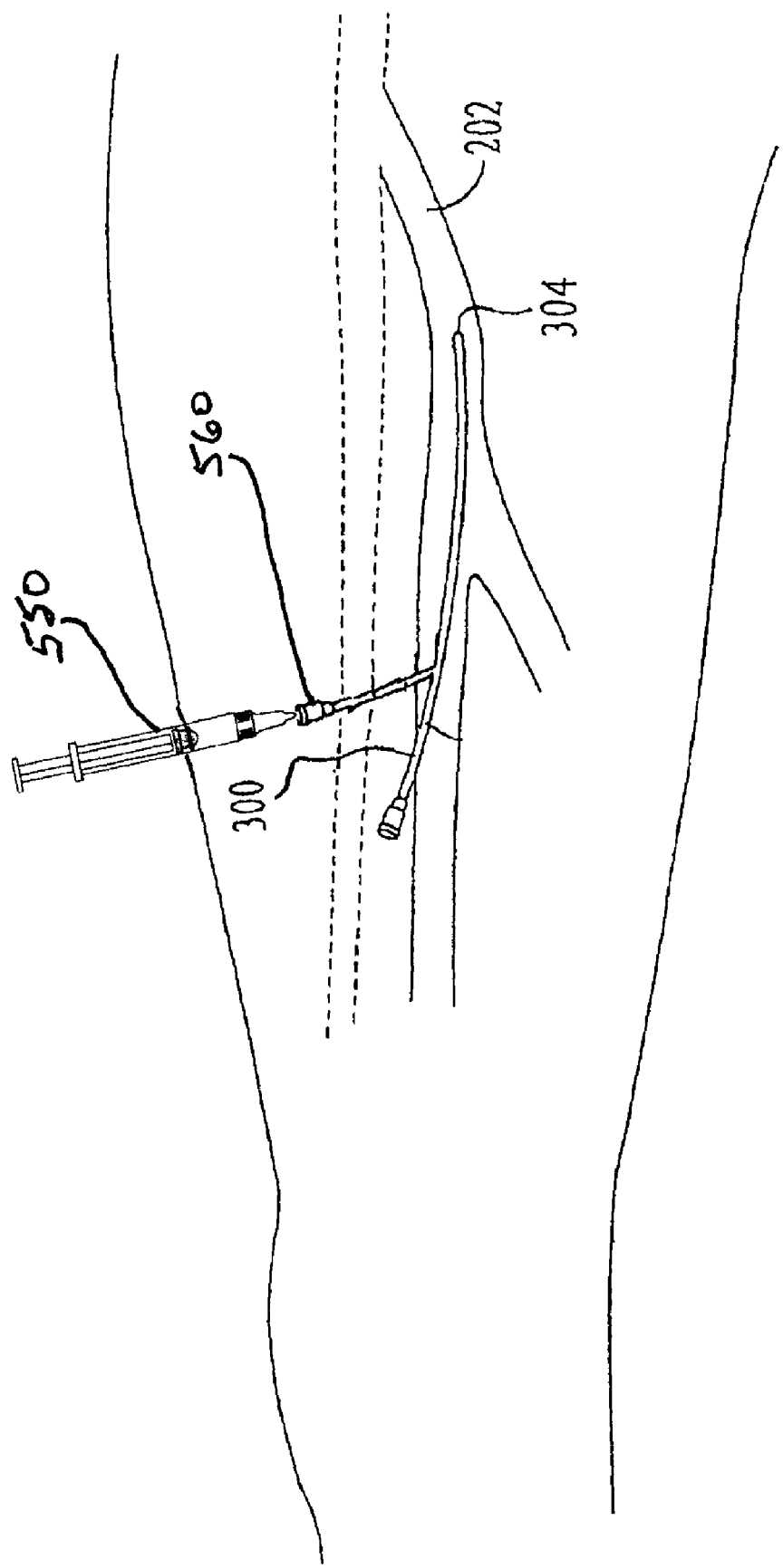
FIG. 8 is an illustration of the leg of a patient shown in FIG. 2, further illustrating the use of a suction device on a port of the introducer sheath.

Next, a suction device, such as a spring loaded syringe 550, is attached to an access port 560 in the sheath 300. See FIG. 8. Alternatively, the suction device may be connected via a separate port if a small access device is used. Once attached, the suction device 550 is used to create a vacuum force that acts to suction out any remaining blood from the vein, completely collapsing the vein around the sheath 300.

Figure 9:
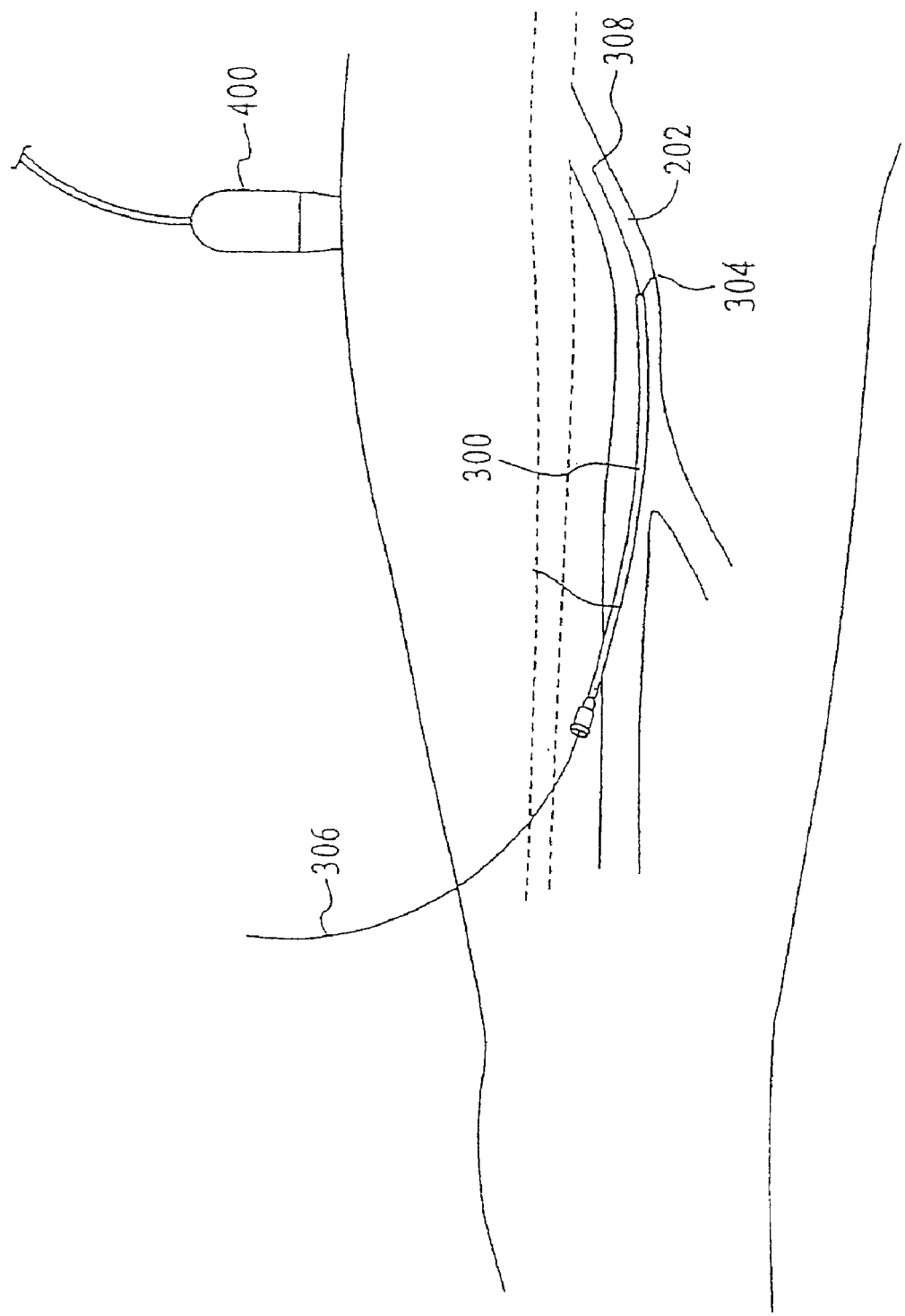
FIG. 9 is an illustration of the leg of a patient shown in FIG. 2, further illustrating the use of an ultrasound device.

An ultrasound handpiece 400, which is used for locating the vein and the fiber 306, can be used to compress the vein and force blood out. See FIG. 9. This process also provides a real time visualization of the effectiveness of the drainage process. For example, when pressure is placed on the skin with the ultrasound head 400, the vein will change size if it has not been completely compressed. Accordingly, if the vein is visualized under the ultrasound and is shown not to change size under compression, this will serve as an indicator that the vein has been completely compressed and contains no more blood.

Once all of the blood is removed, as evidenced by the vein being completely collapsed under ultrasound examination, then tumescent anesthesia is injected around the vein to provide a heat sink. Much less tumescent anesthesia is used in the present method relative to the conventional methods, since the only purpose of the tumescence is to provide a heat sink around the vein. In particular, the tumescent anesthesia is not needed for the vein compression and blood extraction, as taught, for example, in the Goldman et al. patent. Only 150 to 200 ml of tumescence is needed and a positive pressure is no longer needed around the vein compression. The vein has been previously compressed far beyond what can be done with tumescence alone. Reducing the amount of tumescence relative to the prior art procedures also reduces the risk of lidocane reaction in the patient. There is typically a small but significant risk of lidocane overdose in sensitive patients. It is generally accepted in the field that using less than 200 ml of tumescence is adequate for local anesthesia, and as a heat sink, but is not enough to contribute to vein compression.

The endovenous laser ablation procedure can now proceed according to its normal process. For example, the laser ablation procedures described in either of the Navarro et al. patent, the Goldman et al. patent, the Hennings et al. publication, or, most preferably, the U.S. patent application (Ser. No. 60/946, 679) filed on the same date as the present application on behalf of the assignee of the present application, can be used to ablate the vein. All of the external compression is removed during the laser ablation. Since there is now a complete lack of blood in the vein, there is no need for continued manual compression during the laser exposure.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. An endovenous method of treating a varicose vein of a patient, the method comprising using a laser having a wavelength between about 1.2 and 2.5 um to heat and shrink collagen in an exsanguinated varicosed vessel, the laser energy transmitted via fiber optic laser delivery device directly into the varicosed vein.

2. The method of claim 1, wherein blood is removed from the vein by placing the patient in the Trendelenburg position.

3. The method of claim 1, wherein a leg of the patient is wrapped in a flexible bandage, thereby forcing blood out of the vein.

4. The method of claim 1, wherein the vein is massaged externally by hand to exsanguinate blood from the vein.

5. The method of claim 1, wherein the leg is cooled, thereby causing the vein to constrict.

6. The method of claim 1, wherein an ultrasound handpiece is used to compress the vein and visually determine if any blood is left in the vein.

7. The method of claim 1, wherein the vein is caused to spasm, thereby causing constriction of the vein.

8. The method of claim 7, wherein the vein spasm is caused by vibrating or moving a catheter when it is inside the vein.

9. The method of claim 1, wherein a vasoconstricting drug is applied near the vein, thereby causing the vein to constrict.

10. The method of claim 9, wherein said vasoconstricting drug comprises epinephrine.

11. The method of claim 1, wherein a suction device is used to remove blood from the vein.

12. The method of claim 3, wherein said flexible bandage is removed after the blood is removed from the vein, after tumescent anesthesia is injected, and prior to an endovenous laser ablation being performed on said vein.

13. The method of claim 1, wherein a femoral block is injected into the leg of the patient.

14. An endovenous method of treating a varicose vein of a patient, the method comprising using a laser having a wavelength between about 1.2 and 2.5 um to heat and shrink collagen in a varicosed vessel, the laser energy transmitted via fiber optic laser delivery device directly into the varicosed vein from which blood has been sufficiently drained.

15. The method of claim 14, wherein blood is removed from the vein by placing the patient in the Trendelenburg position.

16. The method of claim 14, wherein a leg of the patient is wrapped in a flexible bandage, thereby forcing blood out of the vein.

17. The method of claim 16, wherein said flexible bandage is removed after the blood is removed from the vein, after tumescent anesthesia is injected, and prior to an endovenous laser ablation being performed on said vein.

18. The method of claim 14, wherein the vein is massaged externally by hand to exsanguinate blood from the vein.

19. The method of claim 14, wherein the leg is cooled, thereby causing the vein to constrict.

20. The method of claim 14, wherein an ultrasound handpiece is used to compress the vein and visually determine if any blood is left in the vein.

21. The method of claim 14, wherein the vein is caused to spasm, thereby causing constriction of the vein.

22. The method of claim 21, wherein the vein spasm is caused by vibrating or moving a catheter when it is inside the vein.

23. The method of claim 14, wherein a vasoconstricting drug is applied near the vein, thereby causing the vein to constrict.

24. The method of claim 23, wherein said vasoconstricting drug comprises epinephrine.

25. The method of claim 14, wherein a suction device is used to remove blood from the vein.

26. The method of claim 14, wherein a femoral block is injected into the leg of the patient.

* * * * *